United States Patent [19]

Winters et al.

[11] 4,024,149
[45] May 17, 1977

[54] 2-PHENYL-PYRAZOLO-[1,5-A]QUINOLINE COMPOUNDS

[75] Inventors: Giorgio Winters; Gianfranco Odasso; Giulio Galliani; Leonard J. Lerner, all of Milan, Italy

[73] Assignee: Gruppo Lepetit S.p.A., Milan, Italy

[22] Filed: Oct. 22, 1975

[21] Appl. No.: 624,614

[30] Foreign Application Priority Data

Nov. 23, 1974 United Kingdom ............. 50853/74

[52] U.S. Cl. ................... 260/288 CF; 260/283 SY; 260/287 CF; 260/287 K; 260/288 R; 260/308 R; 260/310 R; 260/310 C; 260/325 R; 424/258; 424/273
[51] Int. Cl.² ...................................... C07D 471/04
[58] Field of Search ............... 260/288 CF, 287 CF; 424/258

[56] References Cited

OTHER PUBLICATIONS

Elguero et al.; Chem. Abst., vol. 74; 87887u (1971).
Elguero et al.; Chem. Abst., vol. 71: 112853c (1969).

*Primary Examiner*—Donald G. Daus
*Assistant Examiner*—Mary C. Vaughn
*Attorney, Agent, or Firm*—Theodore Post; C. Kenneth Bjork

[57] ABSTRACT

New heterocyclic compounds represented by the following formula:

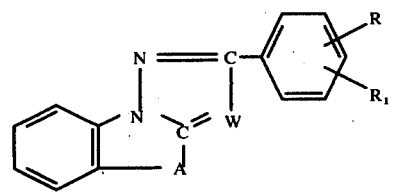

wherein:
R and $R_1$ are independently selected from hydrogen, hydroxy, $(C_{1-4})$alkyl, $(C_{1-4})$alkoxy, $(C_{3-5})$alkenyloxy, $(C_{3-5})$alkynyloxy, $(C_{3-6})$cycloalkyloxy, or halo or taken together represent a methylenedioxy group; the symbols W and A are defined as follows:

1. W is the nitrogen atom and A is the group

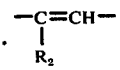

in which the carbon atom bearing the radical $R_2$ is linked to the benzene ring and $R_2$ is hydrogen, hydroxy, $(C_{1-4})$alkoxy or $(C_{2-4})$aliphatic acyloxy;

2. W is the group =CH— and A is —$CH_2$—, —$CH_2$—$CH_2$— or —CH=CH—.

The compounds have antireproductive utility.

5 Claims, No Drawings

2-PHENYL-PYRAZOLO-[1,5-A]QUINOLINE COMPOUNDS

SUMMARY OF THE INVENTION

The present invention is concerned with new heterocyclic compounds represented by the following formula:

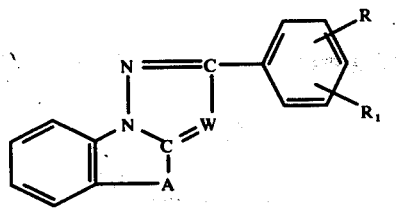

wherein:

R and $R_1$ are independently selected from hydrogen, hydroxy, ($C_{1-4}$) alkyl, e.g., methyl, ethyl, propyl, isopropyl, butyl, isobutyl or tert-butyl; ($C_{1-4}$)alkoxy, e.g., methoxy, ethoxy, propoxy, isopropoxy, butoxy, isobutoxy or tert-butoxy; ($C_{3-5}$)alkenyloxy, e.g., allyloxy, 2-butenyloxy, isobutenyloxy, 3pentenyloxy, 1,1-dimethyl-2-propenyloxy or 3-methyl-2-butenyloxy; ($C_{3-5}$)alkynyloxy, e.g., propargyloxy, 2-butynyloxy, 2-pentynyloxy, 1-methyl-2-propynyloxy, 3-methyl-2-butynyloxy or 4-pentynyloxy; ($C_{3-6}$)cycloalkyloxy, e.g., cyclopropyloxy, cyclobutyloxy, cyclopentyloxy or cyclohexyloxy; benzyloxy; halo, e.g., fluoro, chloro, bromo; or, taken together, represent a methylenedioxy group; the symbols W and A are defined as follows:

1. W is the nitrogen atom and A is the group

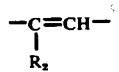

in which the carbon atom bearing the radical $R_2$ is linked to the benzene ring and $R_2$ is hydrogen, hydroxy, ($C_{1-4}$)alkoxy as above defined or ($C_{2-4}$)aliphatic acyloxy, e.g., acetoxy, propionyloxy, butyryloxy or isobutyryloxy;

2. W is the group =CH— and A is —CH$_2$—, —CH$_2$—CH$_2$— or —CH=CH—.

A preferred group of compounds of the above formula comprises those wherein the symbol A represents —CH$_2$—CH$_2$— or —CH$_2$—, W is =CH—, $R_1$ is hydrogen and R is selected from hydrogen, ($C_{1-4}$)alkoxy and benzyloxy. A most preferred group of compounds comprises those wherein the symbol A is —CH$_2$—CH$_2$—, W is =CH—, $R_1$ is hydrogen and R is selected from hydrogen, ($C_{1-4}$)alkoxy and benzyloxy.

DESCRIPTION OF SOME PREFERRED EMBODIMENTS

The compounds of the above formula I can be prepared according to different procedures, which essentially depend on what the pair of symbols W and A are. As an example illustrative of one aspect of the present invention, the compounds of formula I, wherein W is the nitrogen atom and A is the group

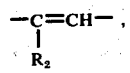

which are triazolo[1,5-a]quinoline derivatives of the following formula

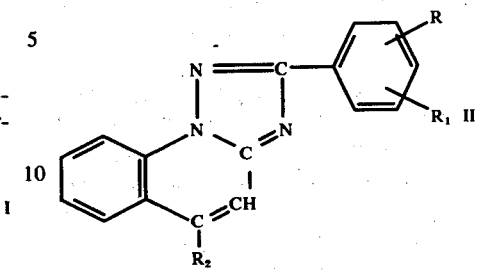

wherein R, $R_1$ and $R_2$ are as above defined, are conveniently prepared via a route which involves as the first step the reaction between a hydrazide of a benzimidic acid of the following general formula:

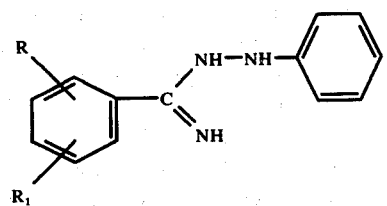

or an acid addition salt thereof, wherein R and $R_1$ are as above defined, with a compound of the formula

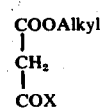

wherein X stands for halo, e.g., chloro or bromo, and Alkyl represents a saturated aliphatic radical of 1 to 4 carbon atoms. The so obtained intermediate triazole of the formula

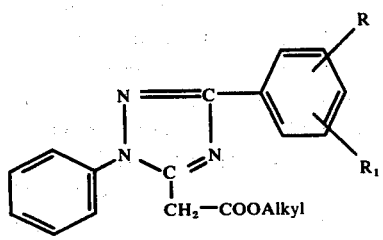

wherein R, $R_1$ and Alkyl are as above defined, is then subjected to alkaline hydrolysis whereby the corresponding free acid of the formula

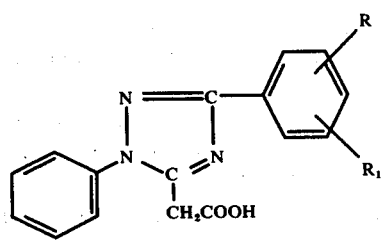

is obtained, which is in turn cyclized by means of an acidic condensing agent to the compound of formula II wherein $R_2$ is hydroxy.

In actual practice, the starting compounds of formulas III and IV are contacted in substantially equimolar ratios, in the presence of an inert organic solvent which is generally selected from one of the halogenated hydrocarbons having 1 to 4 carbon atoms.

If the compound of formula III is employed as an acid addition salt, then a corresponding molar equivalent of a base, e.g., a tertiary organic nitrogen-containing base such as, for instance, trimethylamine, triethylamine, pyridine, picoline or the like is added to the reaction mixture to set free the corresponding base. Said mixture is kept at about room temperature with stirring for about 7 to 10 hours, then is allowed to stand overnight, again at about room temperature. Although not strictly required, the hydrogen halide which forms during this step is preferably blocked by adding to the reaction mixture a further molar equivalent of a tertiary organic nitrogen-containing base, as above defined.

The resulting compound of formula V can be isolated and characterized, if desired, but it is more advantageously employed as such for the subsequent hydrolysis step, which is carried out under alkaline conditions at about room temperature. The so obtained compound of formula VI is finally cyclized to the end product of formula II wherein $R_2$ is hydroxy by means of a suitable acidic condensing agent such as, for instance, polyphosphoric acid, phosphorus pentoxide, boron trifluoride, aluminum trichloride, sulfuric acid or the like.

When in the above reported formula II $R_2$ is hydroxy, the corresponding compound can also exist in the tautomeric keto-form. As a matter of fact, the chemico-physical data, especially the proton magnetic resonance spectrum, point to an enol-form rather than a keto-form.

The compound of formula II wherein $R_2$ is hydroxy, obtained according to the above mentioned process, may undergo subsequent transformations involving the $R_2$ group through which its derivatives falling within the scope of formula II can be prepared. Thus, for instance, the reaction of the hydroxy compounds with zinc powder and mercuric chloride under acidic conditions affords the compounds of formula II wherein $R_2$ is hydrogen, whereas the reaction of the hydroxy compounds with an anhydride derived from a carboxylic aliphatic acid containing from 2 to 4 carbon atoms yields the compounds of formula II wherein $R_2$ is $(C_{2-4})$aliphatic acyloxy. Finally, compounds of formula II wherein $R_2$ is $(C_{1-4})$alkoxy can easily be obtained by treating the said compounds wherein $R_2$ is hydroxy with a suitable alkyating agent as, for instance, a di-$(C_{1-4})$alkyl sulfate or a $(C_{1-4})$alkyl halide.

The starting compounds of formula III are prepared by known procedures, for example as described in Belgian Pat. No. 786,562.

As a further example illustrative of another aspect of the invention, the compounds of formula I wherein W is the =CH— group and A is selected from —CH$_2$—, —CH$_2$—CH$_2$13 or —CH=CH—, which are, respectively, pyrazolo[1,5-a]indoles of the formula

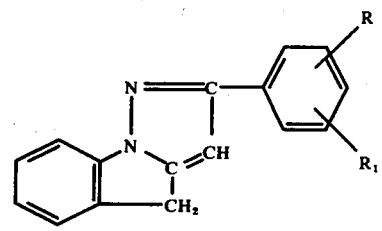

or 4,5-dihydro-pyrazolo[1,5-a]quinolines of the formula

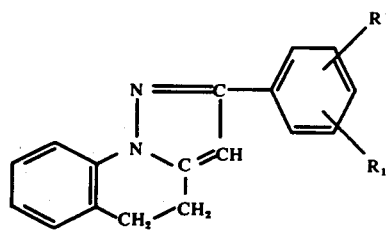

or pyrazolo[1,5-a]quinolines of the formula

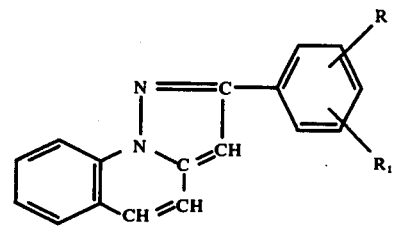

in which R and $R_1$ have the above given meanings, can advantageously be prepared through another scheme, which essentially consists in reacting a compound of the formula

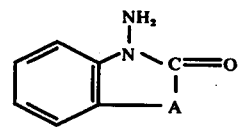

or an acid addition salt thereof, wherein A is —CH$_2$— or —CH$_2$—CH$_2$—, with a 62-ketoester of the formula

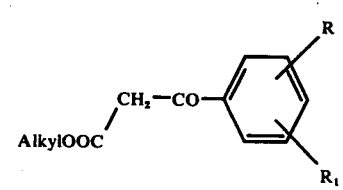

wherein R and $R_1$ have the foregoing meanings and Alkyl represents $(C_{1-4})$alkyl, and cyclizing the so-obtained intermediate of the formula

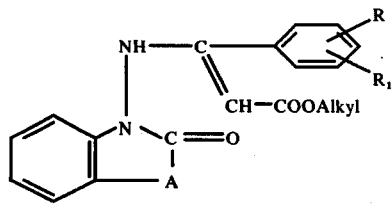

or the corresponding tautomeric iminic form, wherein R and $R_1$ have the foregoing meanings, A is —$CH_2$— or —$CH_2$—$CH_2$—, and Alkyl is as above defined, to a compound of the formula

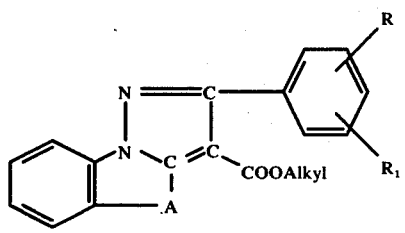

The so-obtained substance is first subjected to a hydrolysis under alkaline conditions and then to thermal decarboxylation so that the compounds of formula VII or VIII are recovered, depending on which substrate of formula X is selected as the starting material.

In actual practice, the starting compounds represented by formulas X and XI are contacted in substantially equimolar ratios in the presence of an inert organic solvent such as, for example, benzene, toluene, dioxane, tetrahydrofuran or the like, in the further presence of an acidic catalyst such as, for instance, p-toluenesulfonic acid, and the resulting mixture is refluxed for about two hours.

The so-obtained intermediate of formula XII, which if desired, can be purified, isolated and characterized, and which proves to be a mixture of the tautomeric amino and imino forms, is then treated for from about 20 minutes to about 2 hours with a slight molar excess of an alkali metal $(C_{1-4})$alkoxide or an alkali metal amide at the reflux temperature of the reaction mixture, optionally in an organic solvent, which is advantageously selected from a lower alkanol having from 1 to 4 carbon atoms. The resulting compound of formula XIII is then hydrolysed under alkaline conditions and the resulting free acid is subjected to thermal decarboxylation, thus obtaining the compound of formula VII or VIII, depending on which substrate of formula X is selected as the starting material.

If a compound of formula VIII is prepared according to the above procedure, it can undergo dehydrogenation by heating it in the presence of sulfur, thus obtaining a compound of formula IX. The said compound of formula VIII can also be obtained by subjecting to the afore-recited reaction conditions the hydrolysis product of the compound of formula XIII wherein A is —$CH_2$—$CH_2$—.

The compounds of formula X wherein A is —$CH_2$— are prepared as described by P. W. Neber, Ber. 55, 826, 1922. The compounds of formula X wherein A is —$CH_2$—$CH_2$— are prepared by the procedure of D. L. Hammick et al., Chemistry and Industry, page 251, Feb. 27, 1954.

Some of the compounds of formula I can also be prepared through chemical modifications of other compounds falling within the scope of formula I prepared according to the procedures outlined above. For instance, the compounds wherein R and/or $R_1$ are hydroxy can conveniently be obtained from the corresponding ones wherein R and/or $R_1$ represent benzyloxy by catalytically removing the benzyl group. The so-obtained compounds can subsequently be treated with suitable alkylating, cycloalkylating, alkenylating or alkynylating agents, e.g. $(C_{1-4})$alkyl halides, $(C_{1-4})$diazoalkanes, di-$(C_{1-4})$alkyl sulfates, cycloalkyl halides containing from 3 to 6 carbon atoms, $(C_{3-5})$alkenyl halides or $(C_{3-5})$alkynyl halides, to prepare the corresponding compounds wherein R and/or $R_1$ are $(C_{1-4})$alkoxy, $(C_{3-5})$alkenyloxy, $(C_{3-5})$alkynyloxy or $(C_{3-6})$cycloalkyloxy.

The compounds of the invention are endowed with a remarkable antifertility utility. In particular they show very interesting post-coital-post-implatantion anti-fertility utility at a dosage of 5–10 mg./kg./day when administered subcutaneously or orally to mammals, e.g. rats, hamsters, dogs and monkeys. Moreover, the abortifacient utility of the new compounds is not accompained by unfavorable effects which are usually associated with hormonal substances.

The following additional description and examples further describe the invention and the manner and process of making and using it to enable the art skilled to make and use the same and set forth the best mode contemplated by the inventors of carrying out the invention.

Representative experiments for assessing the antireproductive activity are carried out with, female Syrian golden hamsters weighing 100–130 g. The animals are mated and the presence of sperm in the vagina is taken as evidence of mating. The day sperm are detected is considered day one of pregnancy since in our laboratories and those of other investigators 90–100% of animals that mate as evidenced by vaginal sperm are pregnant. Pregnancy is later confirmed at time of autopsy by presence of fetuses or implantation sites in the uterus. Even if an animal aborts the fetuses, implantation scars still remain as evidence that the animal had been pregnant. Test compounds dissolved or suspended in sesame oil are administered subcutaneously and/or orally in doses of 5 mg./kg. daily for 5 days beginning on day 4 of pregnancy (days 4–8). The animals are autopsied on day 14 of pregnancy and the uteri are examined for evidence of pregnancy: implantation sites, fetal resorptions or live fetuses, hemorrhage, and evidence of abnormalities of the uterus, placenta or fetuses. A compound is considered to be active if there is a reduction of at least 60% of live fetuses in the treated animals and the presence of implantation sites proves the animal to have been pregnant. The compounds of Examples 2, 5, 6, 10, 11, 14 and 15 proved to be active in this test.

The same criteria and conditions are also employed with rats, with the exception that the animals (female Sprague-Dawley rats weighing 200–230 g.) are treated on days 6 through 10 of pregnancy with a screening dose of 10 mg./kg. s.c., and are autopsied on day 16. The compounds of Examples 2, 5, 11, 13, 14 and 15 proved to be active in this test i.e., they were found to cause a reduction of at least 60% of live fetuses in the treated rats.

The compounds of the invention have a very low toxicity, the $LD_{50}$ values being generally higher than 1000 mg./kg. p.o. in mice.

The compounds of the invention may be administered by various routes, e.g. orally, intravenously or intramuscularly, and are compounded into suitable pharmaceutical dosage forms in admixture with organic or inorganic, solid or liquid pharmaceutical excipients. Suitable excipients are selected from talc, propylene glycols, magnesium stearate, starch, stearyl alcohol, gums, benzyl alcohol, white petroleum jelly and the like. The pharmaceutical dosage forms may be, for example, tablets, capsules, dragees, elixirs, syrups, solutions and the like, and contain the usual preserving, stabilizing, wetting and buffering agents. The pharmaceutical preparations are prepared by conventional procedures.

EXAMPLE 1

5-Hydroxy-2-phenyl-1,2,4-triazolo[1,5-a]quinoline

A. A solution of 38 g. (0.227 mole) of the hydrochloride of benzimidic acid phenyl hydrazide, 25 ml. (0.166 mole) of α-chloroformyl acetic acid ethyl ester and 47.5 ml. (0.335 mole) of triethylamine in 420 ml. of methylene chloride is kept at room temperature for about 3 hours, and to it is subsequently added a solution of 38 ml. (0.271 mole) of triethylamine and 25 ml. (0.166 mole) of α-chloroformyl acetic acid ethyl ester in 30 ml. of methylene chloride. The resulting mixture is stirred for about 4 hours and allowed to stand overnight at room temperature. 48 Grams of the crude intermediate compound of formula V, namely 5-carbethoxymethyl-1,3-diphenyl-1,2,4-triazole is so obtained, which is used as such for the subsequent hydrolysis step.

B. A mixture of 48 g. of the compound prepared as in A) and 160 ml. of 1N sodium hydroxide in 580 ml. of ethanol is stirred for about 40 minutes at room temperature, then the solution is concentrated to small volume in vacuo. Upon acidification with a 10% aqueous solution of hydrochloric acid, a precipitate forms which is collected and dried at about 40° C. over phosphorous pentoxide. Yield, 17 g. of 5-carboxymethyl-1,3-diphenyl-1,2,4-triazole, m.p., 120°–122° C. (with decomposition).

C. 20 Grams (0.0719 mole) of the compound obtained as in B) is added to 200 ml. of polyphosphoric acid, the resulting mixture is stirred for 4 hours at 130°–140° C., and poured into 5 liters of ice-water. The so obtained precipitate is recovered by filtration and is subsequently dissolved in 200 ml. of hot dimethylformamide. After filtering, the organic solution is concentrated to dryness in vacuo and the residue which is obtained is recrystallized from a mixture of ethanol and diethyl ether. Yield, 8.8 g. of the title compound, m.p., 340°–342° C.

EXAMPLE 2

2-Phenyl-1,2,4-triazolo[1,5-a]quinoline

Zinc amalgam is prepared by stirring at room temperature for about 5 minutes a suspension of 20 g. of zinc powder and 2 g. of mercuric chloride in 30 ml. of water and 1 ml. of concentrated hydrochloric acid. The obtained amalgam is poured into a flask containing a solution of 4 g. (0.0153 mole) of the compound of Example 1 in 40 ml. of glacial acetic acid and 40 ml. of concentrated hydrochloric acid. The resulting mixture is kept at the boiling point for 27 hours. During this period, 10 ml. of concentrated hydrochloric acid is added after the 7th hour and an amount of zinc amalgam corresponding to that initially employed is added after the 20th hour. After filtering, the filtrate is concentrated to dryness in vacuo and the resulting residue is taken up with chloroform and chromatographed on silica gel.

Upon eluting with chloroform, the title compound is recovered which is recrystallized from methanol. Yield, 1.0 g., m.p., 137°–139° C.

EXAMPLE 3

5-Acetoxy-2-phenyl-1,2,4-triazolo[1,5-a]quinoline 0.8 Gram (0.00306 mole) of the compound of Example 1 is dissolved in 10 ml. of pyridine, then 1 ml. of acetic acid anhydride is added and the resulting mixture is kept at room temperature for about 12 hours. The obtained precipitate is purified by column chromatography and eluting with a mixture of chloroform:methanol=98.2. After recrystallization from a mixture of methanol and methylene chloride, 0.200 g. of the title compound is obtained, m.p. 200°–202° C.

EXAMPLE 4

5-Methoxy-2-phenyl-1,2,4-triazolo[1,5-a]quinoline

One gram (0.00383 mole) of the compound of Example 1 is dissolved at 60° C. in 30 ml. of dimethylformamide, the resulting solution is brought to room temperature, then 0.2 g. of a 50% oily suspension of sodium hydride is added. After 1 hour, 0.25 ml. (0.004 mole) of methyl iodide is added and the obtained mixture is stirred for 5 hours and concentrated to dryness. The obtained residue is taken up with water and recrystallized from ethanol. Yield, 0.55 g., m.p., 144°–145° C.

EXAMPLE 5

4,5-Dihydro-2-phenyl-pyrazolo[1,5-a]quinoline

A. A mixture of 3.24 g. (0.020 mole) of 1-amino-1,2,3,4-tetrahydroquinoline-2-one, 4.23 g. (0.022 mole) of α-benzoyl ethyl acetate and 0.25g. of p-toluenesulfonic acid in 50 ml. of benzene is refluxed for 6 hours, cooled and washed with sodium bicarbonate and subsequently dried over sodium sulfate. The solvent is then evaporated off and the obtained oily residue is chromatographed on silica gel and eluted with benzene:acetone=90:10 (v/v). Yield, 5.3 g., b.p., 200° C./0.2 mm Hg.

The compound is β-[(2-oxo-1,2,3,4-tetrahydroquinolinyl)amino]-cinnamic acid ethyl ester.

B. 3.6 Grams (0.0107 mole) of the compound prepared as in A) is dissoved in 75 ml. of absolute ethanol and to the resulting solution is added 0.59 g. (0.0112 mole) of sodium methoxide. The mixture is stirred for 1 hour, then is allowed to stand overnight at room temperature. A compound crystallizes which is recovered by filtration. Yield 1.5 g. m.p. 111°–113° C. The compound is 3-carbethoxy-4,5-dihydro-2-phenyl-pyrazolo[1,5-a]quinoline.

C. A solution in 50 ml. of absolute ethanol of 3.18 g. (0.01 mole) of the compound prepared as in B) and 20 ml. of NaOH 1N is refluxed for 3 hours. After standing overnight at room temperature, one distills off the ethanol and the remaining solution is acidified with 10% aqueous hydrochloric acid. The precipitate which forms is recrystallized from acetone. Yield, 2.4 g., m.p., 245°–247° C.

The compound is 3-carboxy-4,5-dihydro-2-phenyl-pyrazolo[1,5-a]quinoline.

D. 5.0 Grams (0.0173 mole) of the acid prepared as in C) is poured into a Kugelrohr apparatus, melted and kept at the melting temperature for about 40 minutes. The oily residue is distilled under reduced pressure thus giving 3.6 g. of the little compound, b.p., 180° C./0.2 mm Hg.

EXAMPLES 6–9

The following compounds are prepared according to the four-step procedure of the foregoing Example.

6. 2-(m-Anisyl)-4,5-dihydropyrazolo[1,5-a]quinoline. M.p. 76°–79° C. (from methanol).
7. 2-(m-Benzyloxyphenyl)-4,5-dihydropyrazolo[1,5-a]quinoline. M.p. 83–4° C. (from methanol).
8. 2-Phenyl-4H-pyrazolo[1,5-a]indole. M.p. 82°–3° C. (from ethanol).
9. 2-(m-Anisyl)-4H-pyrazolo[1,5-a]indole. M.p. 94°–96° C. (from diethyl ether/light petroleum).

EXAMPLE 10

2-(3-Hydroxyphenyl)-4,5-dihydro-pyrazolo[1,5-a]quinoline.

5.0 Grams (0.0142 mole) of the compound of Example 7 is catalytically hydrogenated in 500 ml. of absolute ethanol at room temperature, for 7 hours, in the presence of 1.0 g. of 10% palladium on charcoal as the catalyst. The catalyst is then filtered off, the filtrate is evaporated to dryness, and the obtained residue is recrystallized from methanol. 3.5 Grams of the title compound is obtained, m.p. 172°–175° C.

EXAMPLE 11

2-(m-Ethoxyphenyl)-4,5-dihydropyrazolo[1,5-a]-quinoline 2.62 Grams (0.010 mole) of the compound of Example 10 is added to a solution of 0.23 g. (0.010 mole) of sodium in 40 ml. of absolute ethanol at room temperature, then 2.2 g. ( 0.020 mole) of ethyl bromide is added dropwise. The resulting solution is refluxed for seven hours and allowed to stand overnight at room temperature. After dilution with 30 ml. of water and subsequent evaporation of the ethanol, a residue is obtained which is crystallized from methanol. Yield 2.29 g. of the title compound, m.p. 99°–100° C.

EXAMPLE 12

4,5-Dihydro-2-(m-propoxyphenyl)pyrazolo[1,5-a]quinoline

The title compound is prepared according to the procedure of the foregoing Example, by using propyl chloride as the alkylating agent. B.p., 210° C./0.2 mm. Hg.

EXAMPLE 13

2-(m-Anisyl)pyrazolo[1,5-a]quinoline 2.9 Grams (0.0105 mole) of the compound of Example 6 and 0.5 g. (0.0152 mole) of sulfur are heated at about 260° C. for 25 minutes. Upon distillation under reduced pressure, a product is obtained which is taken up with diethyl ether and the solid which forms is recrystallized from methanol. Yield, 2.04 g. of the title compound, m.p. 82°–84° C.

EXAMPLE 14

2-Phenyl-pyrazolo[1,5-a]quinoline

This compound is obtained according to the procedure of the foregoing Example, starting with the compound of Example 5. M.p., 85°–88° C. (from methanol.)

EXAMPLE 15

2-Phenylpyrazolo[1,5-a]quinoline

One gram (0.00345 mole) of the compound prepared as in C) of Example 5 and 0.2 (0.00625 mole) of sulfur are heated at 260° C. for 30 minutes. Upon distillation under reduced pressure, a product is recovered which is dissolved in methylene chloride. To the resulting solution is added 5 ml. of methanol, the methylene chloride is evaporated off, and the title compound crystallized out. Yield, 0.56 g., m.p. 85°–86° C.

Typical other compounds which are prepared pursuant to the procedures outlined in the above reported Examples are summarized in the following table.

| Basic heterocyclic structure | R / R₁ |
|---|---|
| 4H-pyrazolo[1,5-a]indole | m-tolyl |
| " | 3,4-dimethyl phenyl |
| " | 3-ethylphenyl |
| " | 3-isobutyloxy-phenyl |
| " | 4-isobutenyloxy-phenyl |
| " | 4-(3-pentenyloxy) phenyl |
| " | 3-propargyloxy-phenyl |
| " | 3-(4-pentynyloxy)-phenyl |
| " | 3-cyclopentyloxy-phenyl |
| " | 3-chlorophenyl |
| " | 3,4-dichloro-phenyl |
| " | 2,4-dichloro-phenyl |
| " | 3-(3-methyl-4-chloro)phenyl |
| 4,5-dihydropyrazolo[1,5-a]quinoline | m-tolyl |
| " | p-tolyl |
| " | 3,4-dimethyl-phenyl |
| " | 4-(tert-butoxy)-phenyl |
| " | 3-allyloxy-phenyl |
| " | 3-(3-pentenyloxy)-phenyl |
| " | 4-(1,1-dimethyl-2-propenyloxy)-phenyl |
| " | 4-(2-pentynyloxy)-phenyl |
| " | 3-(4-pentynyloxy)-phenyl |
| " | 4-(4-pentynyloxy)-phenyl |
| " | 4-cyclopropyloxy-phenyl |
| " | 3-chlorophenyl |
| " | 3,4-dichloro-phenyl |
| " | 3,5-dichloro-phenyl |
| " | 3,4-methylene-dioxyphenyl |
| pyrazolo[1,5-a]quinoline | m-tolyl |
| " | p-tolyl |
| " | 3,4-dimethyl- |

| Basic heterocyclic structure | 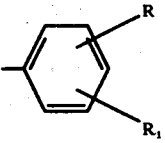 |
|---|---|
| " | phenyl |
| " | 3-propoxyphenyl |
| " | 4-isopropoxyphenyl |
| " | 3-allyloxyphenyl |
| " | 4-(2-butenyloxy)-phenyl |
| " | 3-propargyloxyphenyl |
| " | 4-propargyloxyphenyl |
| " | 4-(2-butynyloxy)-phenyl |
| " | 4-(1-methyl-2-propynyloxy)-phenyl |
| " | 3-cyclopropyloxyphenyl |
| " | 4-cyclopentyloxyphenyl |
| " | 4-cyclohexyloxyphenyl |
| " | 3-chlorophenyl |
| " | 4-chlorophenyl |
| " | 3,4-dichlorophenyl |
| " | 3,4-methylenedioxyphenyl |

PREPARATION OF STARTING MATERIALS

Preparation of the starting materials of formulas II, IV, X and XI:

A. Benzimidic acid phenyl hydrazide hydrochloride This compound is prepared according to the procedure described in Belgian Pat. No. 786,562. M.p. 124° C.

B. 1-Amino-2,3-dihydro-indole-(1,1H)-one This compound is prepared as described by P. W. Neber, Ber. 55, 826, 1922. M.p. 126°–27° C.

C. 1-Amino-1,2,3,4-tetrahydro-quinoline-2-one This compound is prepared as described by D. L. Hammic et al., Chemistry and Industry, page 251, Feb. 27, 1954. M.p. 143° C.

D. (m-Anisoyl)acetic acid ethyl ester This compound is described by J. Clark et al., Journ. Chem. Soc., Sec. C, 1971, 1945. B.p. 162°–66° C./2.5 mm Hg.

E. (m-Benzyloxybenzoyl)-acetic acid ethyl ester This compound is described by W. Bolhofer, Journ. Am. Chem. Soc., 75, 4469, 1953. B.p. 150° C./micropressure.

F. Benzoylacetic acid ethyl ester Commercial product.

G. (α-Chloroformyl)-acetic acid ethyl ester Commercial product.

What is claimed is:

1. A compound represented by the formula

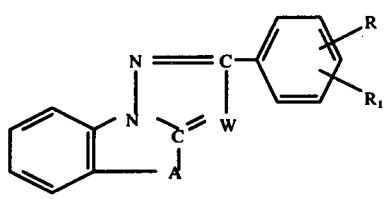

wherein;

R and $R_1$ are independently selected from hydrogen, hydroxy, $(C_{1-4})$ alkyl, $(C_{1-4})$alkoxy, $(C_{3-5})$alkenyloxy, $(C_{3-5})$alkynyloxy, $(C_{3-6})$cycloalkyloxy, benzyloxy, fluoro, chloro and bromo or taken together represent a methylenedioxy group;

W represents the group =CH— and A is selected from —$CH_2$—$CH_2$— and —CH=CH—.

2. A compound as claimed in claim 1 wherein $R_1$ represents hydrogen, R represents hydrogen, $(C_{1-4})$-alkoxy or benzyloxy, W represents the group =CH— and A is —$CH_2$—$CH_2$—.

3. A compound as claimed in claim 1 wherein $R_1$ represents hydrogen, R represents hydrogen, $(C_{1-4})$-alkoxy or benzyloxy, W represents the group =CH— and A represents the group —$CH_2$—$CH_2$—.

4. The compound of claim 1 which is 2-phenyl-pyrazolo[1,5-a]quinoline.

5. A pharmaceutical composition having antireproductive activity containing as the active ingredient an antireproductive amount of a compound as defined in claim 1 together with a suitable pharmaceutical carrier.

* * * * *

UNITED STATES PATENT AND TRADEMARK OFFICE
CERTIFICATE OF CORRECTION

PATENT NO. : 4,024,149
DATED : May 17, 1977
INVENTOR(S) : Giorgio Winters, et al.

It is certified that error appears in the above-identified patent and that said Letters Patent are hereby corrected as shown below:

Column 1, line 26, "3pentenyloxy," should read --3-pentenyloxy,--.

Column 3, line 58, "kyating" should read --kylating--.

Column 3, line 66, "$-CH_2-CH_2 13$" should read -- $-CH_2-CH_2-$ --.

Column 4, line 55, "62-ketoester" should read --β-ketoester--.

Column 6, line 19, "post-coital-post-implatantion- should read --post-coital-post-implantation--.

Column 6, line 24, "pained" should read --panied--.

Column 7, line 42, "phosphorous" should read --phosphorus--.

Column 8, line 53, "dissoved" should read --dissolved--.

Column 9, line 7, "little" should read --title--.

Column 10, line 19, "crystallized" should read --crystallizes--.

UNITED STATES PATENT AND TRADEMARK OFFICE
CERTIFICATE OF CORRECTION

PATENT NO. : 4,024,149

DATED : May 17, 1977

INVENTOR(S) : Giorgio Winters, et al.

It is certified that error appears in the above-identified patent and that said Letters Patent are hereby corrected as shown below:

Column 11, line 38, "1-Amino-2,3-dihydro-indole-(1,1H)-one" should read --1-Amino-2,3-dihydro-indole-(2,1H)-one--.

Column 11, line 42, "Hammic" should read --Hammick--.

Signed and Sealed this

First Day of November 1977

[SEAL]

Attest:

RUTH C. MASON
Attesting Officer

LUTRELLE F. PARKER
Acting Commissioner of Patents and Trademarks